(12) United States Patent
Devereaux (10) Patent No.: US 9,089,198 B1
(45) Date of Patent: Jul. 28, 2015

(54) MEDICAL DEVICE CONCEALMENT AND SECUREMENT DEVICES AND METHODS OF USE

(71) Applicant: Sharon Cantieri Devereaux, Oakdale, CA (US)

(72) Inventor: Sharon Cantieri Devereaux, Oakdale, CA (US)

(*) Notice: Subject to any disclaimer, the term of this patent is extended or adjusted under 35 U.S.C. 154(b) by 0 days.

(21) Appl. No.: 14/157,147

(22) Filed: Jan. 16, 2014

Related U.S. Application Data (60) Provisional application No. 61/850,341, filed on Feb. 12, 2013.

(51) Int. Cl.
| | |
|---|---|
| A45F 5/00 | (2006.01) |
| A61M 25/02 | (2006.01) |
| A61M 27/00 | (2006.01) |
| A45F 5/02 | (2006.01) |
| A61M 1/00 | (2006.01) |
| A61F 5/44 | (2006.01) |
| A45F 3/00 | (2006.01) |

(52) U.S. Cl.
CPC ............ *A45F 5/022* (2013.01); *A45F 2003/002* (2013.01); *A45F 2005/006* (2013.01); *A61F 5/4408* (2013.01); *A61M 1/0019* (2013.01); *A61M 25/02* (2013.01); *A61M 2025/0206* (2013.01)

(58) Field of Classification Search
USPC ......... 224/257, 258, 682, 600, 623, 625, 930; D3/224, 327
See application file for complete search history.

(56) References Cited

U.S. PATENT DOCUMENTS

| | | | | |
|---|---|---|---|---|
| 739,166 | A * | 9/1903 | Funk | 2/102 |
| 1,110,694 | A * | 9/1914 | Jennings | 224/602 |
| 3,659,319 | A * | 5/1972 | Erickson | 24/304 |
| 3,809,349 | A * | 5/1974 | Baedke | 248/51 |
| 3,862,709 | A * | 1/1975 | Roshaven | 224/264 |
| 3,931,917 | A * | 1/1976 | Zellmer | 224/602 |
| 4,069,955 | A * | 1/1978 | Noyes | 224/604 |
| 4,369,946 | A * | 1/1983 | Palmer et al. | 248/74.2 |
| 4,392,858 | A * | 7/1983 | George et al. | 604/133 |
| 4,411,267 | A * | 10/1983 | Heyman | 607/149 |
| 4,634,031 | A * | 1/1987 | Frankhouse | 224/602 |
| 4,722,464 | A * | 2/1988 | Wright | 224/602 |
| 4,793,486 | A * | 12/1988 | Konopka et al. | 206/438 |
| D315,640 | S * | 3/1991 | Pelzel | D3/230 |
| 5,211,321 | A * | 5/1993 | Rodriguez | 224/604 |
| 5,234,420 | A * | 8/1993 | Horton et al. | 604/345 |
| D348,565 | S * | 7/1994 | Cummins | D3/215 |
| 5,643,233 | A * | 7/1997 | Turner | 604/332 |
| 5,688,248 | A * | 11/1997 | Lessing, Jr. | 604/179 |
| 5,758,809 | A * | 6/1998 | Bonner | 224/259 |
| 5,776,105 | A * | 7/1998 | Corn | 604/174 |

(Continued)

*Primary Examiner* — Justin Larson
(74) *Attorney, Agent, or Firm* — Carr & Ferrell LLP (57) ABSTRACT

Medical device concealment and securement devices are provided herein. A scarf device may include a body portion having a first end and a second end spaced apart from one another, the body portion comprising a front side and a back side, the body portion being defined by an outer peripheral edge, and a first plurality of pockets formed near the first end of the body portion, a second plurality of pockets formed near the second end of the body portion, where each of the first and second plurality of pockets being configured to receive and retain a medical device, and a first plurality of securement members disposed on the outer peripheral edge of the first end and proximate the first plurality of pockets, and a second plurality of securement members disposed on the outer peripheral edge of the second end and proximate the second plurality of pockets.

16 Claims, 5 Drawing Sheets

(56) References Cited

U.S. PATENT DOCUMENTS

| | | | |
|---|---|---|---|
| 6,129,709 A * | 10/2000 | Millen | 604/179 |
| 6,270,485 B1 * | 8/2001 | Ekey | 604/345 |
| 6,296,164 B1 * | 10/2001 | Russo | 224/602 |
| 6,610,032 B1 * | 8/2003 | Prody | 604/179 |
| 7,927,311 B1 * | 4/2011 | Bachelder | 604/179 |
| 8,225,973 B1 * | 7/2012 | Bellinson | 224/602 |
| D695,490 S * | 12/2013 | Lake | D2/502 |
| 2005/0072820 A1 * | 4/2005 | Hardison | 224/257 |
| 2012/0091181 A1 * | 4/2012 | Barnes | 224/600 |

\* cited by examiner

MEDICAL DEVICE CONCEALMENT AND SECUREMENT DEVICES AND METHODS OF USE

CROSS-REFERENCE TO RELATED APPLICATIONS

This non-provisional U.S. patent application claims the priority benefit of U.S. Provisional Application Ser. No. 61/850,341, filed on Feb. 12, 2013, titled "System & Method for the Holding, Concealment, and Efficiency Maximization of Medical Bulb Drains, Medical Waste Bags, and/or Other Medical Devices", which is hereby incorporated by reference herein in its entirety including all references cited therein.

FIELD OF THE INVENTION

The present technology is directed generally to various garments that are configured to receive, conceal, and/or secure various types of medical devices such as medical bulb drains, medical waste bags, and other similar medical devices. Exemplary garments may include, but are not limited to scarfs, belts, and lanyards—just to name a few.

SUMMARY

According to some embodiments, the present technology may be directed to a scarf comprising: (a) a body portion having a first end and a second end spaced apart from one another, the body portion comprising a front side and a back side, the body portion being defined by an outer peripheral edge; (b) a first plurality of pockets formed near the first end of the body portion, the first plurality of pockets being disposed on the front side of the body portion and arranged in a linear pattern; (c) a second plurality of pockets formed near the second end of the body portion, the second plurality of pockets being disposed on the front side of the body portion and arranged in a linear pattern, each of the first and second plurality of pockets being configured to receive and retain a medical device; (d) a first plurality of securement members disposed on the outer peripheral edge of the first end and proximate the first plurality of pockets; and (e) a second plurality of securement members disposed on the outer peripheral edge of the second end and proximate the second plurality of pockets, each of the first and second plurality of securement members being configured to secure a portion of the medical device preventing removal of the medical device from the scarf.

According to some embodiments, the present technology may be directed to a lanyard, comprising: (a) a necklace configured to encircle a neck of an individual; and (b) a plurality of extensions extending from the necklace, each of the plurality of extensions comprising a plurality of securement members positioned along a length of the extension, each of the plurality of securement members capable of securing a medical device thereon.

According to other embodiments, the present technology may be directed to a belt, comprising a strip of material having a front surface, a back surface, a first end and a second end, the first end comprising a plurality of linearly aligned apertures that are configured to cooperate with a fastening device disposed on the second end; and a plurality of pockets disposed on the front surface of the strip of material each of the plurality of pockets being configured to receive and retain a medical device.

BRIEF DESCRIPTION OF THE DRAWINGS

Certain embodiments of the present technology are illustrated by the accompanying figures. It will be understood that the figures are not necessarily to scale and that details not necessary for an understanding of the technology or that render other details difficult to perceive may be omitted. It will be understood that the technology is not necessarily limited to the particular embodiments illustrated herein.

DESCRIPTION OF EXEMPLARY EMBODIMENTS

In the following description, for purposes of explanation, numerous specific details are set forth in order to provide a thorough understanding of the disclosure. It will be apparent, however, to one skilled in the art, that the disclosure may be practiced without these specific details. In other instances, structures and devices are shown at block diagram form only in order to avoid obscuring the disclosure.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the present technology includes articles of clothing or clothing accessories such as scarfs, belts, lanyards, and other similar devices that are provided with pockets to receive and retain medical devices that are being utilized by an individual. The individual may wear an article of clothing of the present technology in order to conceal their medical devices within one or more of the pockets of the article of clothing.

Figure 1:
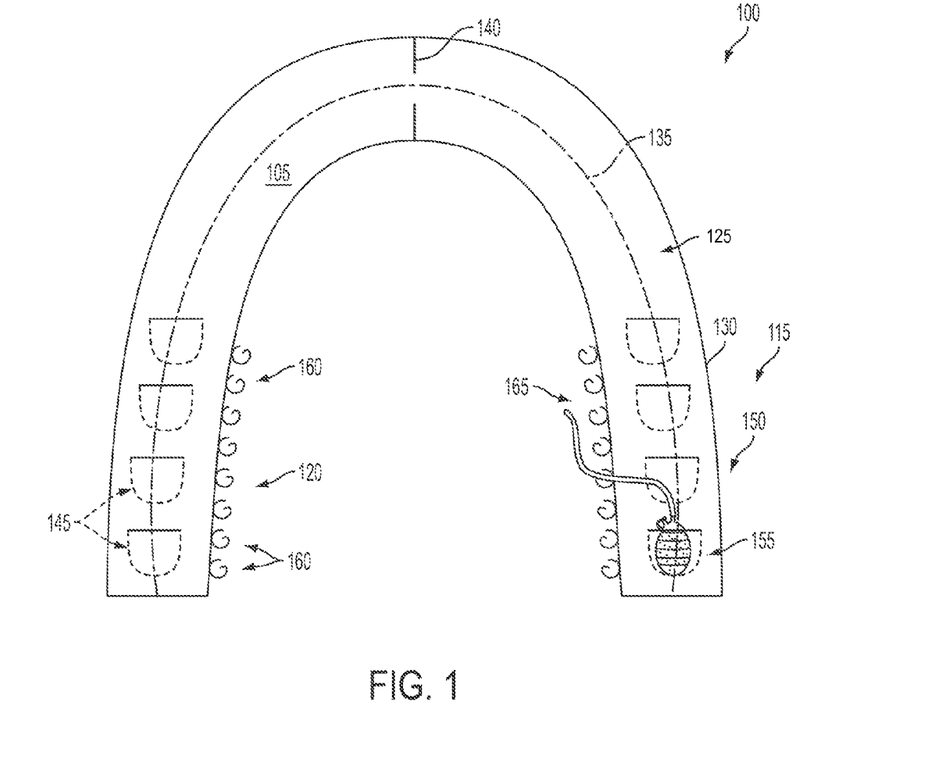
FIG. 1 is a front elevational view of an exemplary scarf, constructed in accordance with the present disclosure.

FIG. 1 is a front elevational view of an exemplary scarf 100, constructed in accordance with the present disclosure. The scarf 100 may comprise a body portion 105, constructed of a strip/length of textile material, although the body portion 105 may be constructed from any suitable material that would be known to one of ordinary skill in the art with the present disclosure before them.

In some embodiments, the body portion 105 generally comprises a first end 115 and a second end 120 that are spaced apart from one another such that the body portion 105 has an overall length. The overall length of the body portion 105 may vary depending upon the size of the individual who will wear or utilize the scarf 100. For example, a taller individual will require a scarf 100 having a body portion 105 with an overall length that is greater than a scarf for a shorter individual. Also, the body portion 105 will have a thickness that will also vary according to design requirements or in accordance with the thickness of the material of the body portion 105.

The body portion 105 includes a front side 125 and a back side (not shown). The shape of the body portion 105 is defined by an outer peripheral edge 130. The body portion 105 also includes a long axis 135 that extends along the overall length of the body portion 105. A short axis 140 of the body portion 105 is oriented perpendicularly to the long axis 135, and roughly corresponds to an overall width of the body portion 105. It is noteworthy that the short axis 140 of the body portion 105 may vary over the length of the body portion 105 if the body portion is not of uniform width.

According to some embodiments, the scarf 100 includes pockets that are disposed on the front side 125 of the body portion 105. In general, each pocket is configured to receive and retain at least a portion of a medical device. A medical device may include any of a medical bulb drain (see FIG. 2), a pump, a monitoring device, a control interface, or any portion of any medical device that is attached, in part, either permanently or temporarily to the individual wearing the scarf 100. Advantageously, the scarf 100 allows for receiving and concealing of the medical device, such that the individual need not carry the medical device by hand or expose the medical device.

In some embodiments, the body portion 105 is provided with a first plurality of pockets 145 formed near the first end 115 of the body portion 105. The first plurality of pockets 145 may be disposed on the front side 125 of the body portion 105. The first plurality of pockets 145 may be arranged in a substantially linear pattern, or the pockets may be offset or staggered relative to one another. The first plurality of pockets 145 of FIG. 1 are shown as being slightly offset from one another.

The body portion 105 also includes a second plurality of pockets 150 formed near the second end 120 of the body portion 105. The second plurality of pockets 150 are disposed in a linear pattern on the front side 125 of the body portion 105 and their placement mirrors that of the first plurality of pockets 145. As mentioned above, each of the first and second plurality of pockets are configured to receive and retain a medical device. For example, a medical bulb drain (e.g., medical device) 155 is disposed within a pocket of the second plurality of pockets 150.

According to some embodiments, the first plurality of pockets 145 may be disposed on the front side 125 of the body portion 105 and the second plurality of pockets 150 may be disposed on the back side of the body portion 105. Indeed, the scarf 100 may include pockets on both the front and back sides of the body portion 105.

The scarf 100 may also include a first plurality of securement members 160 disposed on the outer peripheral edge 130 of the first end 115 and proximate the first plurality of pockets 145. A securement member may include, for example, a clip, a clamp, a tie, a wrap, a grommet, and other similar devices that are capable of receiving and/or securing an object. For example, a securement member may include a clip that receives a portion of the medical device that is secured within one of the pockets. The use of securement members is illustrated and described in greater detail with reference to FIG. 2, which is provided infra.

In some embodiments, the scarf 100 may comprise a second plurality of securement members 165 disposed on the outer peripheral edge 130 of the second end 120 and proximate the second plurality of pockets 150. Generally, each of the first and second plurality of securement members is configured to receive and/or secure a portion of the medical device preventing removal of the medical device from the scarf 100. According to some embodiments, the scarf may include securement members that are disposed anywhere along the outer peripheral edge 130 of the body portion 105. Also, one or more securement members may be disposed on the front or back sides of the body portion 105.

Figure 2:
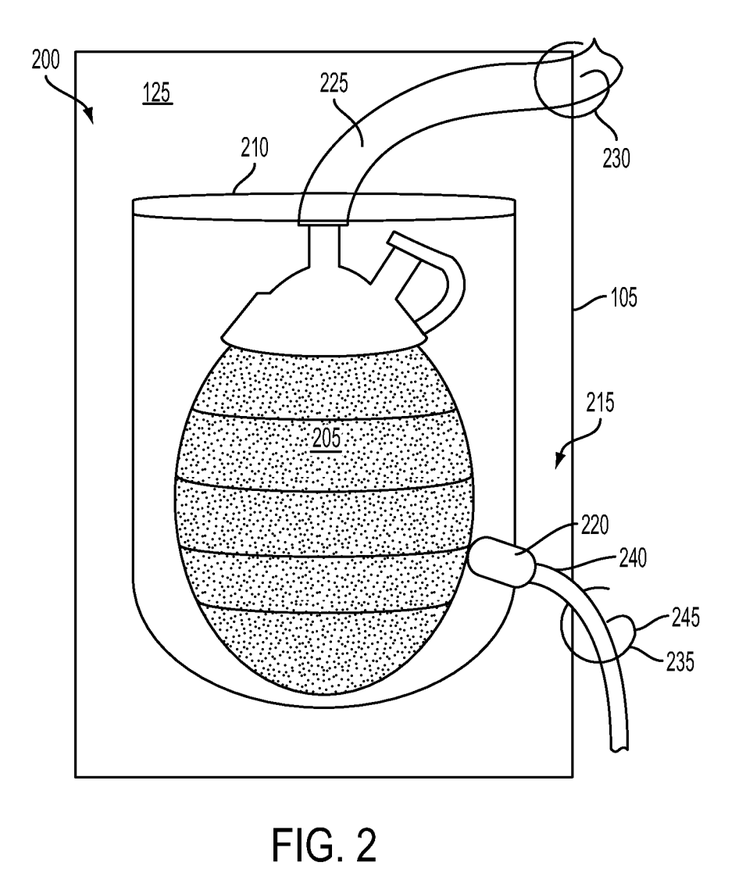
FIG. 2 is a front elevational view of a pocket of the exemplary scarf of FIG. 1, illustrating a medical bulb drain in association with the pocket.

FIG. 2 is a front elevational view of a pocket 200 of the exemplary scarf 100 of FIG. 1, illustrating a medical bulb drain 205 in association with the pocket 200. The pocket 200 comprises a first opening 210 that provides access to an inside portion of the pocket 200. In general, the first opening 210 is sized to allow the medical bulb drain 205 to be inserted within the pocket 200.

According to some embodiments, the pocket 200 may be constructed from a material that is fluid impervious. Therefore, if the medical bulb drain 205 is compromised and leaks, any fluid that may leak from the medical bulb drain 205 is contained within the pocket 200. The pocket 200 may include a complete pocket that is attached to the front side 125 of the body portion 105. In other embodiments, the pocket 200 may be formed by attaching a section of material to the front side 125 of the body portion 105 such that the pocket 200 is formed by the joining of the section of material with the front side 125 of the body portion 105.

The pocket 200 in some instances includes a second opening 215 that is configured to allow at least a portion of the medical bulb drain 205 to extend therethrough. For example, the medical bulb drain 205 may include a drain port 220 that allows the medical bulb drain 205 to be emptied without disconnecting the medical bulb drain from an input drain hose 225. The pocket 200 may also include tertiary or additional openings along the pocket 200. Additionally, the location of the second (or more) openings along the pocket may vary according to design requirements According to some embodiments, each of the first and second plurality of securement members includes a substantially G-shaped clip that has an opening that receives a tube associated with the medical device or a portion of the medical device.

In some instances, the G-shaped clip comprises an inwardly bent end of clip that prevents removal of the tube or the portion of the medical device therefrom.

More specifically, the scarf 100 is shown as comprising two G-shaped clips 230 and 235 (e.g., securement members) disposed proximate the pocket 200. An upper clip 230 receives and secures the input drain hose 225, and a lower clip 235 receives and secures an output drain hose 240 associated with a drain port 220 of the medical bulb drain 205. Because a part (or parts) of the medical bulb drain is secured by the clips, the medical bulb drain may be not be easily or unwantedly removed from the pocket 200. An inwardly bent end 245 of the clip 235 prevents removal of the tube or the portion of the medical device therefrom.

In other embodiments, rather than providing a path for hoses or drains, the second opening 215 may allow for other components such as wire leads, connections, interfaces, or other similar components of a medical device to extend outwardly from the pocket 200.

According to some embodiments, the first opening for the pockets may be substantially oriented parallel to the short axis 140 of the scarf 100, such as shown in FIG. 2. The first opening of a pocket may also be oriented substantially parallel to the long axis 135 of the scarf 100, or may be oriented at any angle relative to the long or short axes of the scarf 100.

In use, when the individual wears the scarf 100 and inserts a medical device into one of the pockets of the scarf 100, the individual may wear the scarf 100 in such a way that the pockets face the torso of the individual, rather than facing the pockets outwardly. This method of wearing the scarf further enhances the concealment of medical device that may be present in the pockets.

Figure 3:
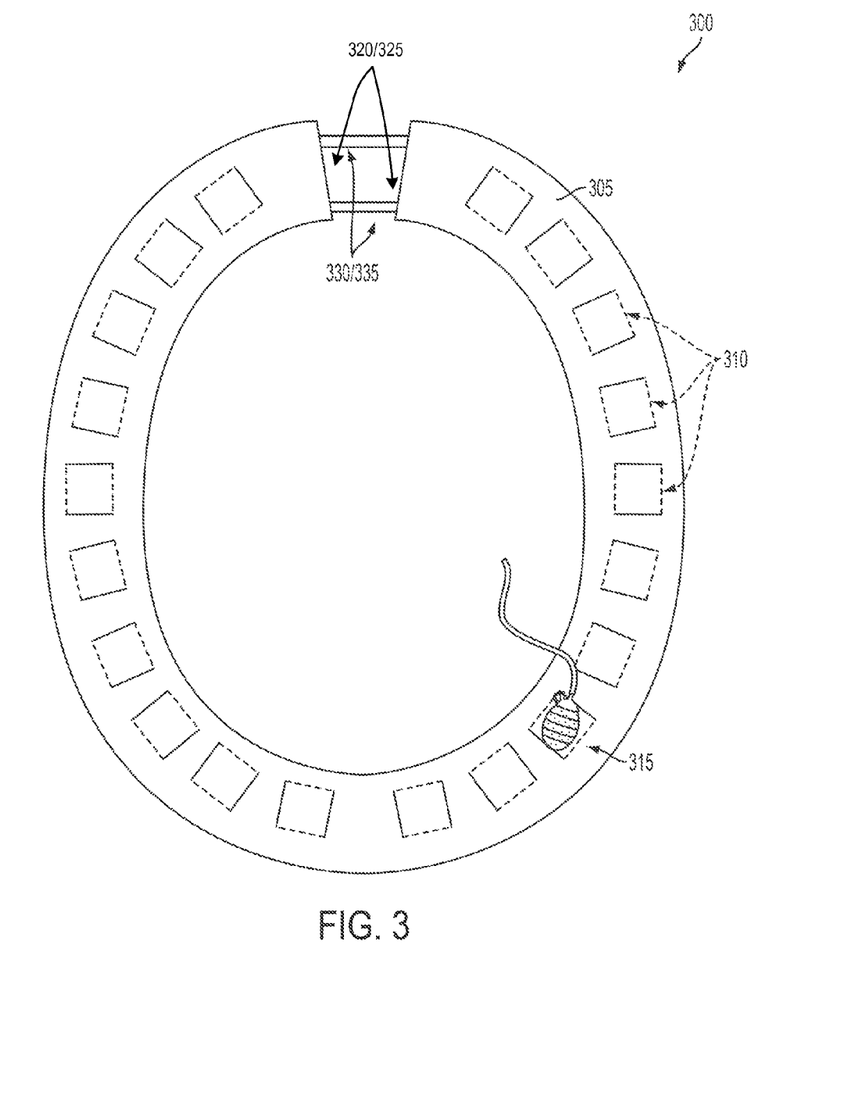
FIG. 3 is a front elevational view of another exemplary scarf that includes adjustable members for varying the diameter of the scarf.

FIG. 3 is a front elevational view of another exemplary scarf 300 that includes adjustable members for varying the diameter of the scarf 300. It is noteworthy that the scarf 300 includes a body portion 305 that is similar to the body portion of the scarf 100 of FIG. 1. The scarf 300 is provided with a plurality of pockets 310 that extend along the entire length of the body portion 305. Each of the pockets 310 is configured to receive and retain a medical device 315.

The scarf 300 comprises two adjustable fasteners 320 and 325, which are each configured to associate with a first end 330 and a second end 335 of the body portion 305 so as to keep the first end 330 and the second end 335 secured around an individual. Also, the fasteners 320 and 325 are adjustable so as to vary a diameter of the scarf 300 when the first and second ends are brought together. Thus, the scarf 300 can be selectively variable with respect to size, to accommodate for individuals of varying size. The adjustable fasteners may include, for example, strips of hook and loop material, ties, strips of material that utilize snaps or buttons for securement, or other similar adjustable devices. Also, the scarf 300 may include more or fewer adjustable fasteners than two.

Figure 4:
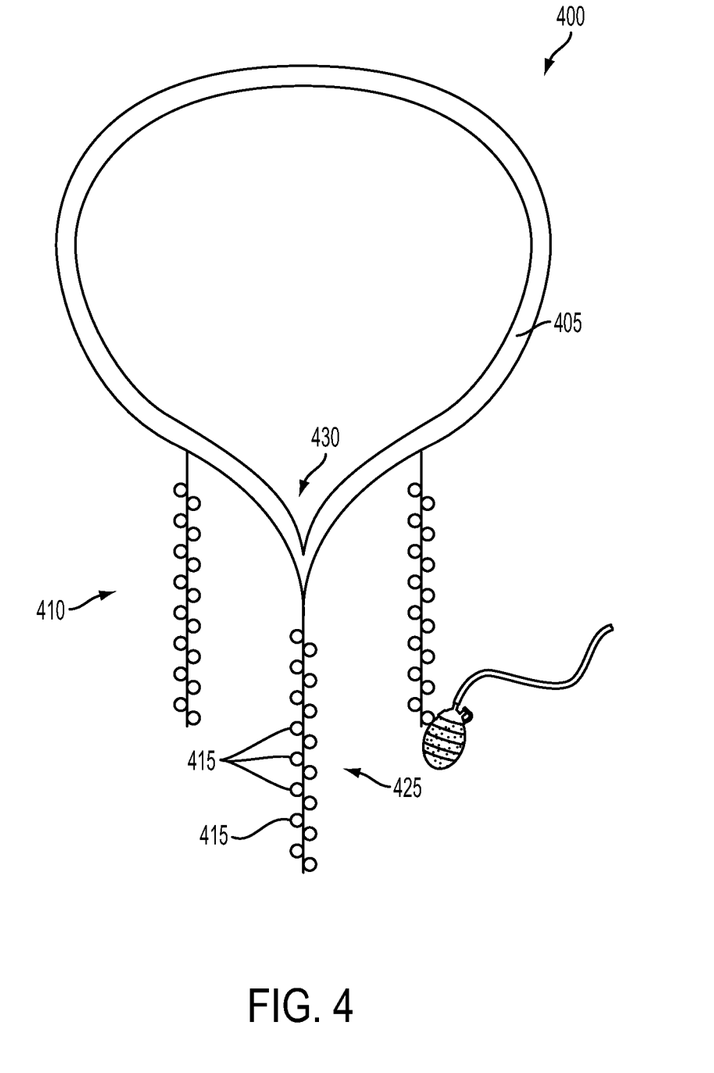
FIG. 4 is a front elevational view of an exemplary lanyard, constructed in accordance with the present disclosure.

FIG. 4 is a front elevational view of an exemplary lanyard 400, constructed in accordance with the present disclosure. The lanyard 400 includes a necklace 405 configured to encircle a neck of an individual. The lanyard 400 also includes a plurality of extensions 410 extending from the necklace 405. It will be understood that each of the plurality of extensions 410 comprises a plurality of securement members 415 positioned along a length of the extension. Advantageously, each of the plurality of securement members capable of securing a medical device thereon. Again, a securement member may include, for example, a clip, a clamp, a tie, a wrap, a grommet, and other similar devices that are capable of receiving and/or securing an object.

According to some embodiments, the plurality of securement members 415 for an extension, such as extension 425 are disposed on opposing sides of the extension 425. In some instances, the securement members 415 on one side of the extension 425 are offset from securement members on an opposing side of the extension 425.

In some embodiments, the necklace 405 has a teardrop shape and one of the plurality of extensions extends from a cusp portion 430 of the necklace 405. The cusp portion 430 allows a center extension to extend lower than the extensions that flank the center extension on the right and left thereof, without requiring the use of extensions of different lengths.

Figure 5:
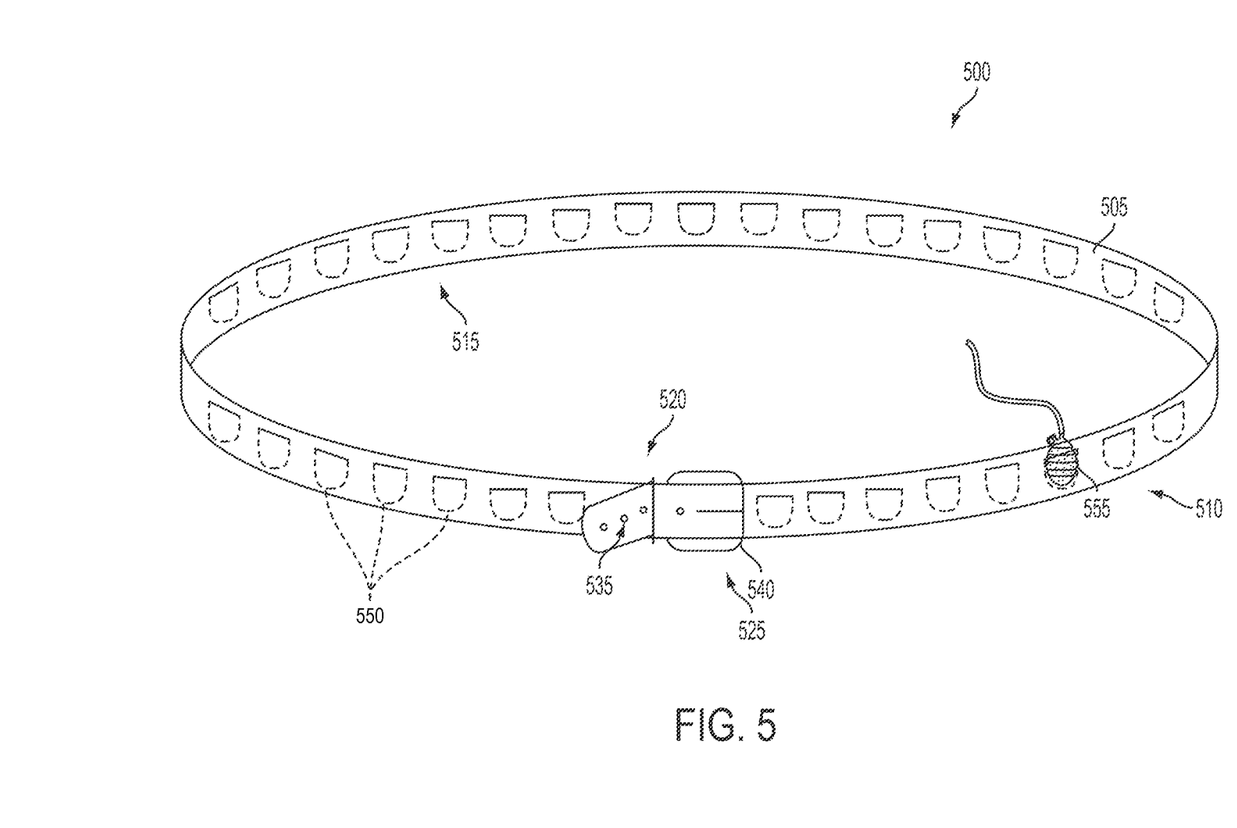
FIG. 5 is a perspective view of an exemplary belt, constructed in accordance with the present disclosure.

FIG. 5 is a perspective view of an exemplary belt 500, constructed in accordance with the present disclosure. In some instances the belt 500 comprises a strip of material 505 having a front surface 510, a back surface 515, a first end 520, and a second end 525.

Generally, the belt 500 is configured such that a first end 520 comprises a plurality of linearly aligned apertures 535 that are configured to cooperate with a fastening device 540 disposed on the second end 525. The fastening device 540 may be a buckle, Velcro, a tie, or any similar device.

According to some embodiments, each of a plurality of pockets 550 are disposed on the front surface 510 of the strip of material 505. As with the scarf 100 described supra, at least a portion of the plurality of pockets of the belt include a second opening that allows at least a portion of the medical device 555 to extend therethrough. Also, the pockets of the belt may include first and second openings that operate in a substantially similar manner to the pockets and openings of the scarf of FIGS. 1 and 2.

While the above embodiments contemplate a scarf, a lanyard, and a belt, one or ordinary skill in the art will appreciate that other articles of clothing and/or accessories may also likewise be constructed in accordance with the present technology.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A scarf, comprising:
    a body portion having a first end and a second end spaced apart from one another, the body portion comprising a front side and a back side, the body portion being defined by an outer peripheral edge;
    a first plurality of pockets formed near the first end of the body portion, the first plurality of pockets being disposed on the front side of the body portion and arranged in a staggered linear pattern;
    a second plurality of pockets formed near the second end of the body portion, the second plurality of pockets being disposed on the front side of the body portion and arranged in a staggered linear pattern, each of the first and second plurality of pockets receiving and retaining a medical device and facing the torso of a user of the scarf when the scarf is worn by the user, enhancing concealment of the medical device;
    a first plurality of securement members disposed on the outer peripheral edge of the first end and proximate the first plurality of pockets; and
    a second plurality of securement members disposed on the outer peripheral edge of the second end and proximate the second plurality of pockets; wherein a number of the first and second pluralities of securement members is greater than a number of the first and second pluralities of pockets; and wherein at least two of the first and second pluralities of securement members secure a portion of the medical device preventing removal of the medical device from the scarf.

2. The scarf according to claim 1, wherein the first plurality of pockets and the second plurality of pockets are disposed along a length of the body portion.

3. The scarf according to claim 1, wherein each of the first plurality of pockets and the second plurality of pockets are constructed from a material that is fluid impervious.

4. The scarf according to claim 1, wherein at least a portion of the first plurality of pockets and the second plurality of pockets each include a second opening that allows at least a portion of the medical device to extend therethrough.

5. The scarf according to claim 1, further comprising two adjustable fasteners, which are each configured to associate with the first end and the second end so as to keep the first end and the second end secured around the neck of an individual, wherein the fasteners are adjustable so as to vary a diameter of the scarf when the first and second ends are brought together around the neck of the individual using the two adjustable fasteners.

6. The scarf according to claim 1, wherein each of the first and second plurality of securement members includes a substantially G-shaped clip that has an opening that receives a tube associated with the medical device or a portion of the medical device, wherein an inwardly bent end of clip prevents removal of the tube or the portion of the medical device therefrom.

7. The scarf according to claim 1, wherein each of the first and second plurality of pockets each include a first opening for receiving the medical device, wherein the first opening is oriented along a long axis of the scarf.

8. The scarf according to claim 1, wherein each of the first and second plurality of pockets each include a first opening for receiving the medical device, wherein the first opening is oriented along a short axis of the scarf.

9. A method for securing a medical device to a user via a scarf worn around the user's neck, the method comprising:
providing a body portion of the scarf having a first end and a second end spaced apart from one another, the body portion comprising a front side and a back side, the body portion being defined by an outer peripheral edge;
providing a first plurality of pockets formed near the first end of the body portion, the first plurality of pockets being disposed on the front side of the body portion and arranged in a staggered linear pattern;
providing a second plurality of pockets formed near the second end of the body portion, the second plurality of pockets being disposed on the front side of the body portion and arranged in a staggered linear pattern to mirror the placement of the first plurality of pockets, each of the first and second plurality of pockets receiving and retaining a medical device and facing the torso of a user of the scarf when the scarf is worn by the user, enhancing concealment of the medical device; and
securing a portion of the medical device to the scarf via at least two of a first plurality of securement members disposed on the outer peripheral edge of the first end and proximate the first plurality of pockets and a second plurality of securement members disposed on the outer peripheral edge of the second end and proximate the second plurality of pockets; wherein a number of the first and second pluralities of securement members is greater than a number of the first and second pluralities of pockets.

10. The method of claim 9, wherein the first plurality of pockets and the second plurality of pockets are disposed along a length of the body portion.

11. The method of claim 9, wherein each of the first plurality of pockets and the second plurality of pockets are constructed from a material that is fluid impervious.

12. The method of claim 9, wherein at least a portion of the first plurality of pockets and the second plurality of pockets each include a second opening that allows at least a portion of the medical device to extend therethrough.

13. The method of claim 9, further comprising:
providing two adjustable fasteners, each configured to associate with the first end and the second end so as to keep the first end and the second end secured around the neck of the user, wherein the fasteners are adjustable so as to vary a diameter of the scarf when the first and second ends are brought together around the neck of the user using the two adjustable fasteners.

14. The method of claim 9, wherein each of the first and second plurality of securement members includes a substantially G-shaped clip that has an opening that receives a tube associated with the medical device or a portion of the medical device, wherein an inwardly bent end of clip prevents removal of the tube or the portion of the medical device from the scarf.

15. The method of claim 9, wherein each of the first and second plurality of pockets each include a first opening for receiving the medical device, and the first opening is oriented along a long axis of the scarf.

16. The method of claim 9, wherein each of the first and second plurality of pockets each include a first opening for receiving the medical device, wherein the first opening is oriented along a short axis of the scarf.

* * * * *